(12) United States Patent
Ding (10) Patent No.: US 9,574,175 B2
(45) Date of Patent: Feb. 21, 2017

(54) ENDOMETRIAL POLYP STEM CELL

(75) Inventor: Dah-Ching Ding, Hualien (TW)

(73) Assignee: Hualien Tzu Chi Hospital, Buddhist Tzu Chi Medical Foundation, Hualien (TW)

(*) Notice: Subject to any disclaimer, the term of this patent is extended or adjusted under 35 U.S.C. 154(b) by 0 days.

(21) Appl. No.: 13/225,911

(22) Filed: Sep. 6, 2011

(65) Prior Publication Data

US 2013/0059373 A1    Mar. 7, 2013

(51) Int. Cl.
| | | |
|---|---|---|
| *C12N 5/074* | (2010.01) | |
| *C12N 5/0775* | (2010.01) | |
| *C12N 5/095* | (2010.01) | |
| *C12N 5/079* | (2010.01) | |
| *C12N 5/077* | (2010.01) | |
| *C12N 5/071* | (2010.01) | |

(52) U.S. Cl.
CPC ........... *C12N 5/0618* (2013.01); *C12N 5/0652* (2013.01); *C12N 5/0682* (2013.01); *C12N 2506/243* (2013.01)

(58) Field of Classification Search
CPC .............................. A61K 35/28; C12N 5/0682
USPC .................................................. 435/325, 366
See application file for complete search history.

(56) References Cited

U.S. PATENT DOCUMENTS

2008/0274087 A1* 11/2008 Li et al. ........................ 424/93.7
2010/0040588 A1*  2/2010 Walton et al. ............... 424/93.7

OTHER PUBLICATIONS

Cui CH, Uyama T, Miyado K, Terai M, Kyo S, Kiyono T, Umezawa A. Menstrual blood-derived cells confer human dystrophin expression in the murine model of Duchenne muscular dystrophy via cell fusion and myogenic transdifferentiation. Mol Biol Cell. May 2007;18(5):1586-94. Epub Feb. 21, 2007.*

(Continued)

*Primary Examiner* — Arthur S Leonard
(74) *Attorney, Agent, or Firm* — Mintz Levin Cohn Ferris Glovsky and Popeo, P.C.; Steven M. Jensen; Richard B. Emmons (57) ABSTRACT

An endometrial polyp stem cell is disclosed in the present invention. The endometrial polyp stem cell is isolated from an endometrial polyp tissue, expresses vimentin, CD13, CD29, CD44, and CD90, and has no expression of CD1q, CD3, CD34, and CD45.

4 Claims, 12 Drawing Sheets

(56) References Cited

OTHER PUBLICATIONS

Kyo S, Nakamura M, Kiyono T, Maida Y, Kanaya T, Tanaka M, Yatabe N, Inoue M. Successful immortalization of endometrial glandular cells with normal structural and functional characteristics. Am J Pathol. Dec. 2003;163(6):2259-69.*
Moon JH, Kwak SS, Park G, Jung HY, Yoon BS, Park J, Ryu KS, Choi SC, Maeng I, Kim B, Jun EK, Kim S, Kim A, Oh S, Kim H, Kim KD, You S. Isolation and characterization of multipotent human keloid-derived mesenchymal-like stem cells. Stem Cells Dev. Aug. 2008;17(4):713-24.*
Ding DC, Shyu WC, Chiang MF, Lin SZ, Chang YC, Wang HJ, Su CY, Li H. Enhancement of neuroplasticity through upregulation of beta1-integrin in human umbilical cord-derived stromal cell implanted stroke model. Neurobiol Dis. Sep. 2007;27(3):339-53. Epub Jun. 18, 2007.*
Xuebing P, TinChiu L, Enlan X, Jing L, Xiaowu H. Is endometrial polyp formation associated with increased expression of vascular endothelial growth factor and transforming growth factor-beta1? Eur J Obstet Gynecol Reprod Biol. Nov. 2011;159(1):198-203. Epub Jul. 2, 2011.*
2012 Merriam-Webster Online Medical Dictionary by Merriam-Webster, Incorporated, Springfield, MA, USA.*
Caroline E. Gargett and Hirotaka Masuda. Adult stem cells in the endometrium. Molecular Human Reproduction, vol. 16, No. 11 pp. 818-834, 2010.*
R Dimitrov, et al., Characterization of clonogenic stromal cells isolated from human endometrium. Reproduction (2008) 135 551-558.*
Antonio Alberto Nogueira, et al.Immunohistochemical expression of p63 in endometrial polyps: evidence that a basal cell immunophenotype is maintained. Menopause. vol. 13. No. S. pp. 826-830.*
Masuda et al., Noninvasive and real-time assessment of reconstructed functional human endometrium in NOD/SCID/gammac null immunodeficient mice. PNAS, Feb. 6, 2007 _ vol. 104 _ No. 6 _ 1925-1930.*
Masuda et al., Stem Cell-Like Properties of the Endometrial Side Population: Implication in Endometrial Regeneration, PLoS ONE. Apr. 2010, vol. 5, Issue 4, p. 1-8.*
Patel et al., Multipotent Menstrual Blood Stromal Stem Cells: Isolation, Characterization, and Differentiation. Cell Transplantation, vol. 17, pp. 303-311, 2008.*
Kato et al., Characterization of side-population cells in human normal endometrium. Human ReprOlluction Vul.22. No. 5 pp. 1214-1223. 2007.*
Arnold et al., Endometrial stromal cells regulate epithelial cell growth in vitro: a new co-culture model. Human Reproduction vol. 16, No. 5 pp. 836-845, 2001.*
Gargett et al., Isolation and Culture of Epithelial Progenitors and Mesenchymal Stem Cells from Human Endometrium. Biology of Reproduction 80, 1136-1145 (2009).*
Meng et al., Endometrial regenerative cells: A novel stem cell population. Journal o(Tronslatioool Medicine 2007. 5:57, pp. 1-10.*
Lonza Inc., Clonetics™ Endothelial Cell System Product Sheet, 2015, pp. 1-15.*
Kim et al., Expression and distribution patterns of the stem cell marker, nestin, and the stem cell renewal factor, BMI-1, in normal human nasal mucosa and nasal polyps. Acta Oto-Laryngologica, 2009, 129:9, 996-1001.*
Wolf et al., Endometrial stem cell transplantation restores dopamine production in a Parkinson's disease model. J. Cell. Mol. Med. vol. 15, No. 4, 2011 pp. 747-755.*
Ding et al., "Enhanced differentiation and clonogenicity of human endometrial polyp stem cells", Differentiation-ISSN 0301-4681, vol. 81, No. 3, pp. 172-180 (2011).

* cited by examiner

ENDOMETRIAL POLYP STEM CELL

SEQUENCE LISTING

The instant application contains a Sequence Listing which has been submitted in ASCII format via EFS-Web, and is hereby incorporated by reference in its entirety. Said ASCII copy, created on Nov. 21, 2011, is named 89264US.txt and is 2456 bytes in size.

BACKGROUND OF THE INVENTION

1. Field of the Invention

The present invention relates to a stem cell, and more particularly, to an endometrial polyp stem cell.

2. Description of Related Art

The human endometrium contains substantial vascularized stroma and regenerates regularly with each menstrual cycle. Previous studies identified stem/progenitor cells residing in the human endometrium (Gargett, 2006). Regeneration initiated by cells in the basalis layer replace cells shed during menstruation. Additionally, colony-forming stem cells were identified in the human endometrium (Schwab and Gargett, 2007).

Stromal or mesenchymal stem cells (MSCs) are self-renewing cells that can differentiate into mesodermally derived tissues and have been identified in several stroma-containing tissues such as bone marrow, adipose tissue, the cord matrix, and skeletal muscle (Ding et al., 2007a). The scientific community has recognized the remarkable developmental/differentiation plasticity of MSCs (Grove et al., 2004), which have garnered considerable attention.

In a culture, MSCs are plastic-adherent, spindle-shaped cells that express a panel of surface markers, including CD105 (endoglin, SH2), CD73 (ecto-50 nucleotidase, SH3, and SH4), CD166 (ALCAM), CD29 (b1-integrin), CD44 (H-CAM), CD90 (Thy-1), and STRO-1. In contrast to hematopoietic stem cells (HSCs), MSCs are negative for CD45, CD34, and CD133 (Jones et al., 2002).

Endometrial polyps are localized hyperplastic overgrowths of endometrial glands and stroma around a vascular core that form a sessile or pedunculated projection from the endometrial surface. Endometrial polyps cause intermenstrual bleeding, irregular bleeding, and menorrhagia (Hillard, 2006).

In the present invention, stem cells have been isolated from endometrial polyps and characterized as MSCs.

SUMMARY OF THE INVENTION

The present invention provides an endometrial polyp stem cell, which is isolated from an endometrial polyp tissue, and expresses vimentin, CD13, CD29, CD44, and CD90.

According to the present invention, the endometrial polyp stem cell has no expression of CD1q, CD3, CD34, and CD45.

In the present invention, the endometrial polyp tissue is obtained from endometrium of a hysterectomy specimen.

In the present invention, the endometrial polyp stem cell has capability to differentiate to an osteoblast-like cell, an adipocyte-like cell and a neural cell.

According to the present invention, the endometrial polyp stem cell has clonogenicity.

BRIEF DESCRIPTION OF THE DRAWINGS

FIG. 3A to FIG. 3D illustrate multilineage differentiation capacity of EPMSCs grown in proliferation medium and in vitro differentiation of EPMSCs to osteocytes, adipocytes and neural cells, wherein

DETAILED DESCRIPTION OF THE PREFERRED EMBODIMENTS

The detailed description of the present invention is illustrated by the following specific examples. Persons skilled in the art can conceive the other advantages and effects of the present invention based on the disclosure contained in the specification of the present invention.

Isolation and Characterization of EPMSCs

The local Research and Ethics Committee approved this study, and informed consent was obtained from each patient prior to tissue harvesting. Endometrial polyp tissue samples were harvested by cutting an endometrial polyp from hysterectomy specimens with a surgical knife (patient age, 40-50 years). Specimens were obtained from women who had not undergone hormone therapy (n=6). All polyps were pathologically proven benign endometrial polyps. Endometrial stromal cells were also obtained from endometrium of hysterectomy specimens collected from women who had not undergone hormone therapy (patient age, 40-50 years) (n=6). Tissue samples were placed in $Ca^{2+}/Mg^{2+}$-free phosphate-buffered saline (PBS), and were then transferred to the laboratory immediately.

Endometrial polyp tissues and endometrium were removed from the transport medium, placed in a Petri dish, and minced into small pieces (1-2 $mm^3$) in the presence of $Ca^{2+}/Mg^{2+}$-free PBS. Tissues were dissociated with 0.5% collagenase (Sigma, US) and 0.05% type-I deoxyribonuclease (Sigma, USA) and incubated for 60 min at 37° C. with gentle pipetting at 15-min intervals. Cell suspensions were filtered through a 40 micrometer sieve (Becton Dickinson, USA) to eliminate aggregated cells, and washed with PBS. The solution containing predominantly endometrial glands was centrifuged, and the supernatant was discarded. The pellet was treated with 0.25% trypsin/0.03% ethylenediaminetetraacetic acid (EDTA) (Sigma, USA) at 37° C. for 10 min, and the reaction was stopped by adding cold Dulbecco's Modified Eagle Medium-low glucose (DMEM-LG) with 10% fetal calf serum (FCS). Cell suspensions were filtered as mentioned and combined. Cells were resuspended in DMEM-LG and centrifuged on a Ficoll-Paque (Pharmacia LKB, Uppsala, Sweden) for 15 min at 500×g to remove erythrocytes. Cells were collected from the interface, washed, and resuspended in DMEM with 10% fetal bovine serum (FBS).

Isolated single endometrial polyp cells and stromal cells were seeded in culture dishes at a density of $1\times10^4$ cells/$cm^2$, which were selected for repeated experiments, in DMEM-LG medium supplemented with 10% FBS, 100 mg/mL penicillin G sodium, and 100 mg/mL streptomycin sulfate. Cultures were incubated at 37° C. under 5% $CO_2$ and 95% humidity. Adherent cells were used for experiments after incubation for 3-4 days. As controls, human bone marrow MSCs (BMSCs) were utilized and cultured in Minimum Essential Medium alpha medium ($\alpha$-MEM) with 15% FBS. To determine the cellular lifespan of endometrial polyp-derived fibroblast-like cells (EPMSCs), primary cells at passage 2 were plated at a density of $3\times10^5$ cells/10-cm dish and passaged every 3 days, followed by the standard 3T3 protocol with a calculation of the number of population doublings daily (You et al., 2004). A cell growth curve was also generated after plating cells at a $10^4$ cells/six-well dish using the conditions described above. Cells were then stained with 0.01% crystal violet solution daily for 6 days. Crystal violet from stained cells was quantified to determine relative cell growth rates.

The specific surface molecules of cells from endometrial polyps in cultures of 4-8 passages were characterized by flow cytometry. Cells were detached with 2 mM EDTA in PBS, washed with PBS containing 2% BSA and 0.1% sodium azide (Sigma, USA), and incubated with the respective antibodies conjugated with fluorescein isothiocyanate (FITC) or phycoerythrin (PE), including CD1q, CD3, CD10, CD13, CD14, CD31, CD34, CD45, CD90, CD73, CD56, HLA-ABC, HLA-DR, CD49b, CD49d, CD29, CD44, CD105, CD117, CD146, and CD166 (BD, PharMingen). Thereafter, cells were analyzed using a Becton Dickinson flow cytometer (Becton Dickinson, San Jose, Calif., USA).

As shown in FIG. 1A, EPMSCs resembled fibroblasts and were similar regardless of patient source. Vimentin immunostaining was utilized to identify cells originated from the mesenchyme. Vimentin was expressed in cells isolated from endometrial polyps, endometrial stroma stem cells (EmSCs), and BMSCs (lower panel in FIG. 1A). As shown in FIG. 1B, the cell population doubled every 31 h. The EPMSCs proliferated faster than EmSCs and BMSCs.

Figure 2A:
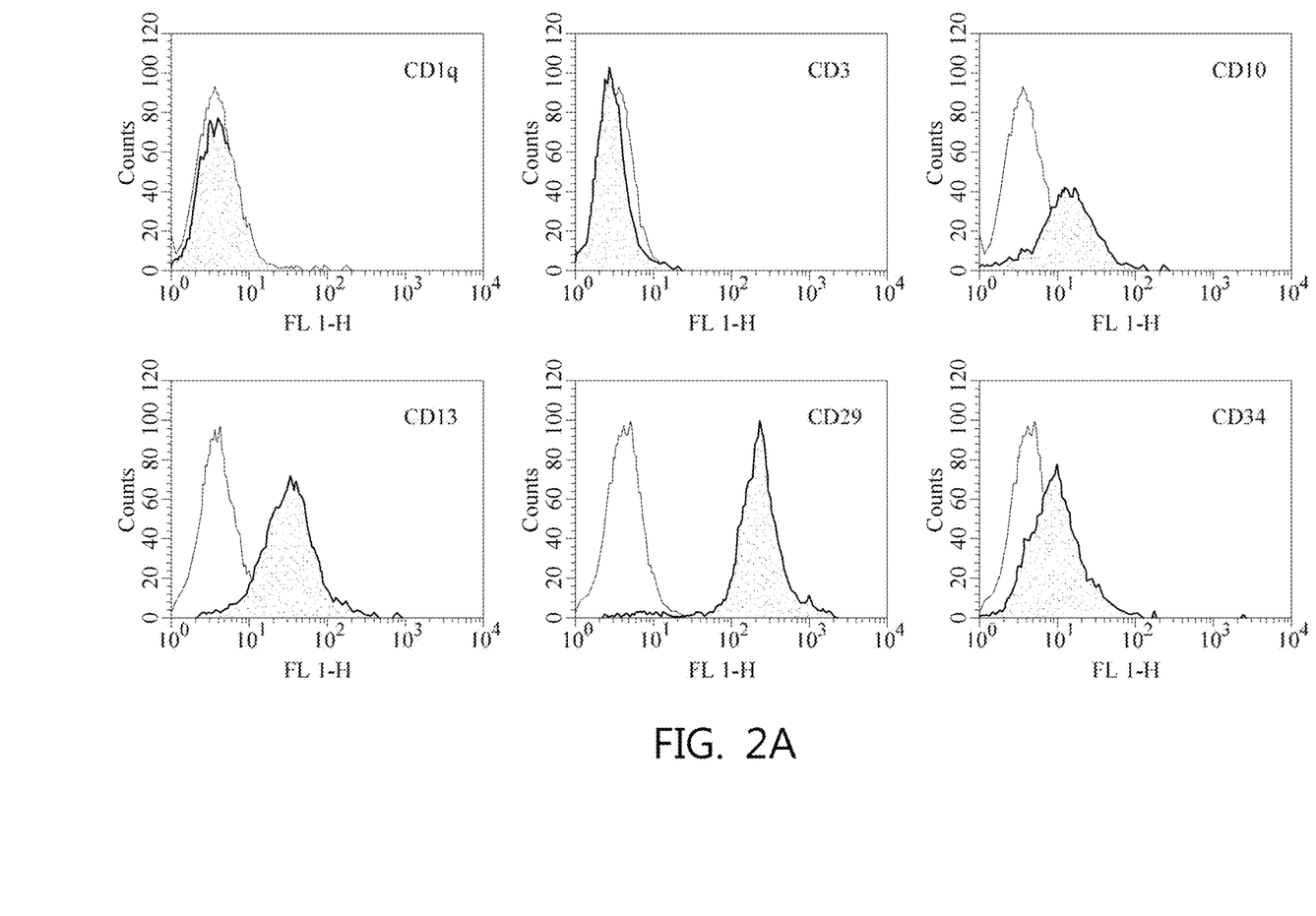
FIG. 2A shows the FACS analysis of EPMSCs and FIG. 2B shows the FACS analysis of BMSCs according to the present invention, wherein cells were labeled with antibodies against hematopoietic antigens (CD1q, CD3, CD34, CD45 and CD117), MSC markers (CD10, CD13, CD29, CD44, CD56, CD90 and CD166) and the endometrial stem cell marker (CD146), and analyzed by flow cytometry.
Figure 2B:
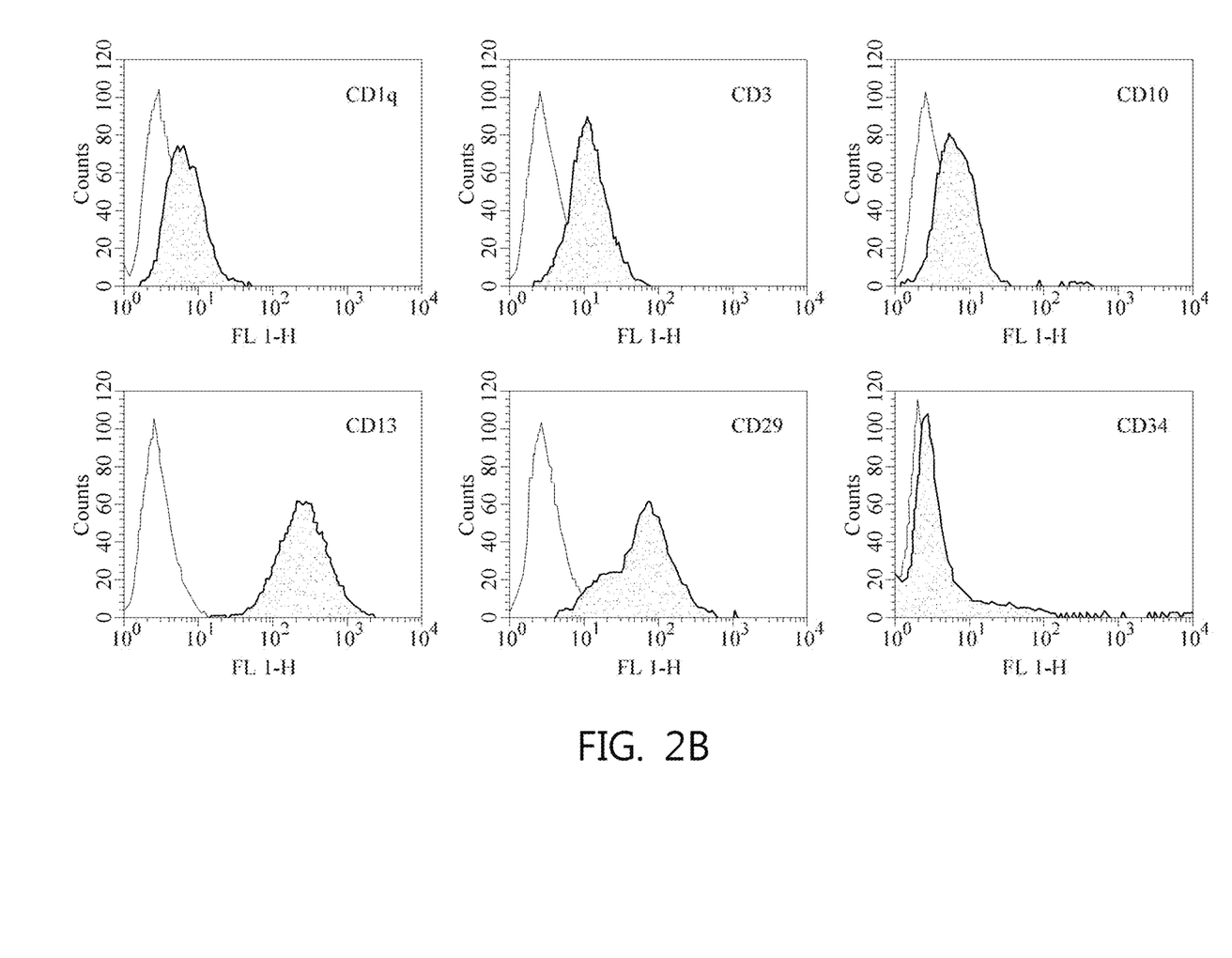

Referring to FIG. 2, the fluorescence activated cell sorting (FACS) analysis using multiple surface markers demonstrates that >90% of EPMSCs and the control BMSCs expressed typical MSC markers CD13, CD29, CD44, and CD90. Conversely, known hematopoietic stem cell (HSCs), neural stem cell (NSCs) and endothelial cell markers, such as CD1q, CD3, CD34, and CD45, were not expressed. Thus, EPMSCs resembled BMSCs, not hematopoietic stem cell or neural stem cell.

In Vitro Differentiation Assay

Endometrial polyp stem cells were passaged, cultured to confluence, and shifted to osteogenic medium (DMEM supplemented with 10% FBS, 0.1 µmol/L dexamethasone, 10 mmol/L $\beta$-glycerol phosphate, and 50 µmol/L ascorbate) and adipogenic medium (DMEM supplemented with 10% FBS, 1 µmol/L dexamethasone, 5 µg/mL insulin, 0.5 mmol/L isobutylmethylxanthine and 60 µmol/L indomethacin) for 3 weeks. The differentiation potential for osteogenesis was assessed by mineralization of calcium accumulation by Alizarin Red S staining. For adipogenic differentiation, intracellular lipid droplets were observed microscopically and confirmed by Oil Red O staining (Lee et al., 2004). For differentiating neural cells, the endometrial polyp stem cells were incubated with DMEM using a three-step method as described previously (D'Ippolito et al., 2004). Briefly, cells were plated at a low density in six-well plates containing fibronectin (10 ng/ml-coated coverslips) in DMEM-LG, 10% FBS with 100 U/ml penicillin and 1 mg/ml streptomycin for 24 h. Neural specification (step 1) was induced by exposing cells to DMEM-LG, 20% FBS, and 10 ng/ml bFGF for 24 h. At the end of neural specification treatment, cells were washed for three times with PBS, and neural commitment (step 2) was then induced by exposing the cells to DMEM-LG, 1 mM $\beta$-mercaptoethanol ($\beta$-ME), and 10 ng/ml neurotrophin-3 (NT-3) for 2 days. Finally, neural differentiation (step 3) was induced by first washing the cells for three times with PBS and then exposing them to NT-3 (10 ng/ml), nerve growth factor (NGF) (10 ng/ml) and brain-derived neurotrophic factor (BDNF) (50 ng/ml) in DMEM-LG for 3-7 days. For spheroid formation, confluent cells were cultured in suspension for 5 days using low-attachment plates to observe their ability to produce spheroids.

Mesenchymal Differentiation Potential of Human EPMSCs

To determine whether the EPMSCs can differentiate into a range of cell types of the mesenchymal lineage, this study examined the potential of EPMSCs to differentiate into osteoblast- and adipocyte-like cells.

Immunocytochemical staining for Nestin, glial fibrillary acidic protein (GFAP), neurofilament 200 kDa (NF200), microtubule associated protein-2 (MAP-2) and neuron-specific class III $\beta$-tubulin (Tuj-1), (dilution 1:200; Chemicon, Temecula, Calif., USA) was utilized to assess the capacity of endometrial polyp stem cells for neuronal differentiation. Vimentin (dilution 1:200; Chemicon, Temecula, Calif., USA) was utilized to identify isolated cells originating from the mesenchyme. Cells were fixed in 4% paraformaldehyde and permeabilized with PBS containing 5% skim milk (Becton, Dickinson, USA) and 0.1% Triton X-100 for 30 min. Cells were then incubated with mouse anti-human monoclonal antibodies overnight. After washing with PBS containing 0.5% Tween 20, cells were incubated with FITC-conjugated secondary antibodies for 30 min. Negative and positive control slides were prepared by incubating sections with isotype controls instead of the primary antibody. Nuclei were counterstained with Hoechst 33342. Cells were then washed for three times with PBS and observed by fluorescence microscopy (Olympus, Tokyo, Japan).

Figure 3:
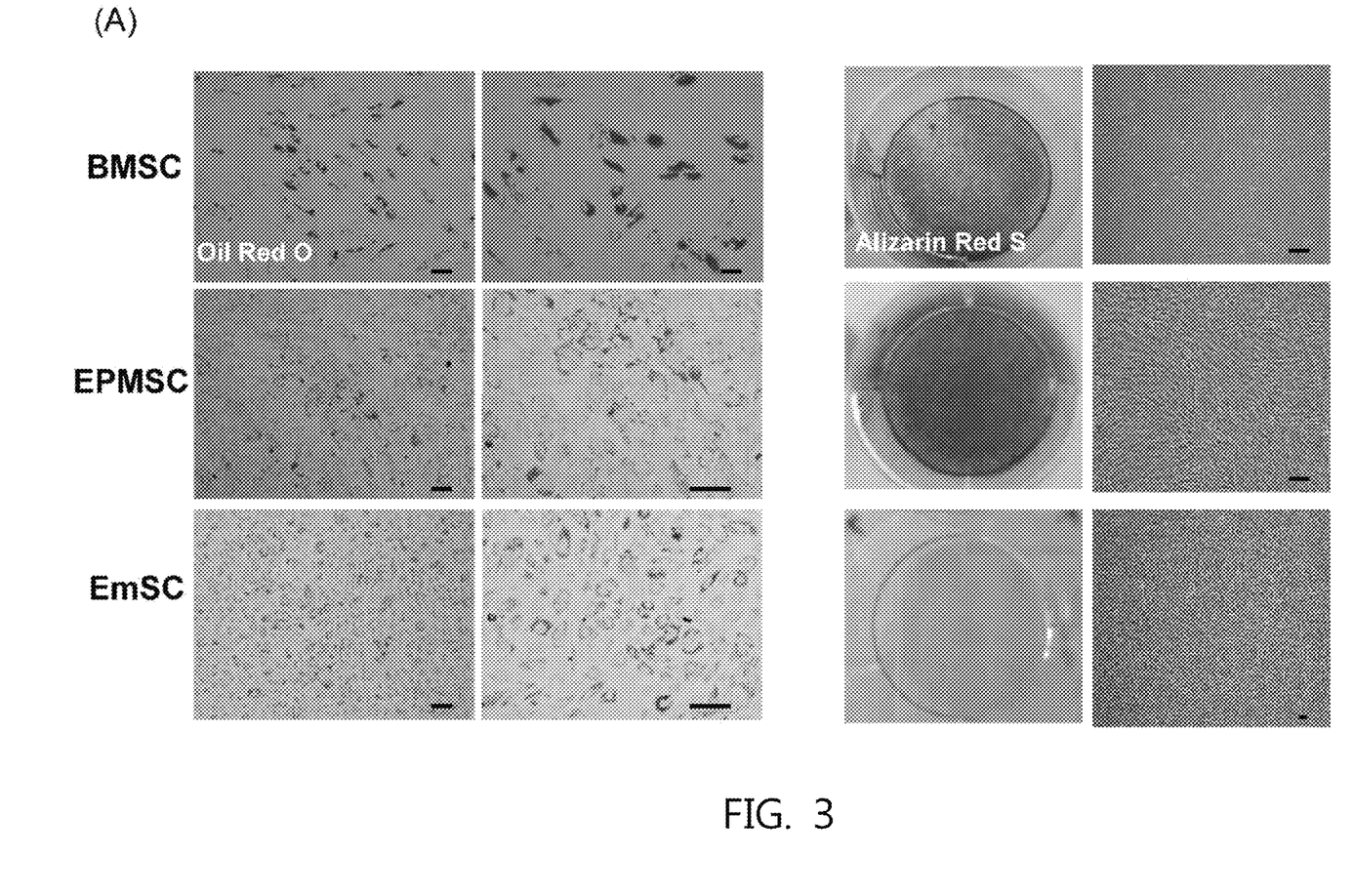
FIG. 3A shows morphological changes in the formation of neutral lipid vacuoles, with almost all cells containing numerous lipid droplets positive with Oil Red-O (left panel) in adipogenic differentiation and shows numerous differentiated cells containing mineralized matrices, which were strongly stained by Alizarin Red-S (right panel) in osteogenic differentiation.
FIG. 3B shows the RT-PCR analysis of adipogenic and osteogenic formula-treated cells for specific genes (PPAR-r and osteopontin) and GAPDH (left panel), and the right panel shows quantitative PCR of these two genes in three types of cells.
FIG. 3C shows in neuro-glial differentiation, morphologies of refractile cell bodies with extended neurite-like structures were arranged into a network, as visualized by phase microscopy, in which the EPMSCs-derived neuroglial cells were identified by immunostaining against Nestin, Tuj-1, NF200, MAP-2 and GFAP, Scale bar=100 μm.
FIG. 3D shows the RT-PCR analysis of specific genes from neurogenic formula-treated cells (Tuj-1, GFAP, MAP2 and nestin)

Under culture in osteogenic induction medium for 2-3 weeks, EPMSCs formed an Alizarin red-positive matrix along the cell membrane that appeared as large red aggregate particles embedded in the extracellular matrix, indicating osteogenic differentiation. Referring to FIG. 3B, the expression of osteopontin was confirmed by RT-PCR analysis. The expression level of osteopontin was high in BMSCs, moderate in EPMSCs and low in EmSCs.

After culturing in adipogenic induction medium for 2 weeks, the differentiated EPMSCs had small oil droplets in their cytoplasm, as demonstrated by Oil Red O staining (as shown in FIG. 3B). Expression of peroxisome proliferators activated receptor r (PPARr) was shown by RT-PCR, demonstrating differentiation into adipogenic lineages. However, the expression level of PPARr was the same for EPMSCs and EmSCs, but lower than that of BMSCs.

Neuronal Differentiation Potential of EPMSCs

Figure 1:
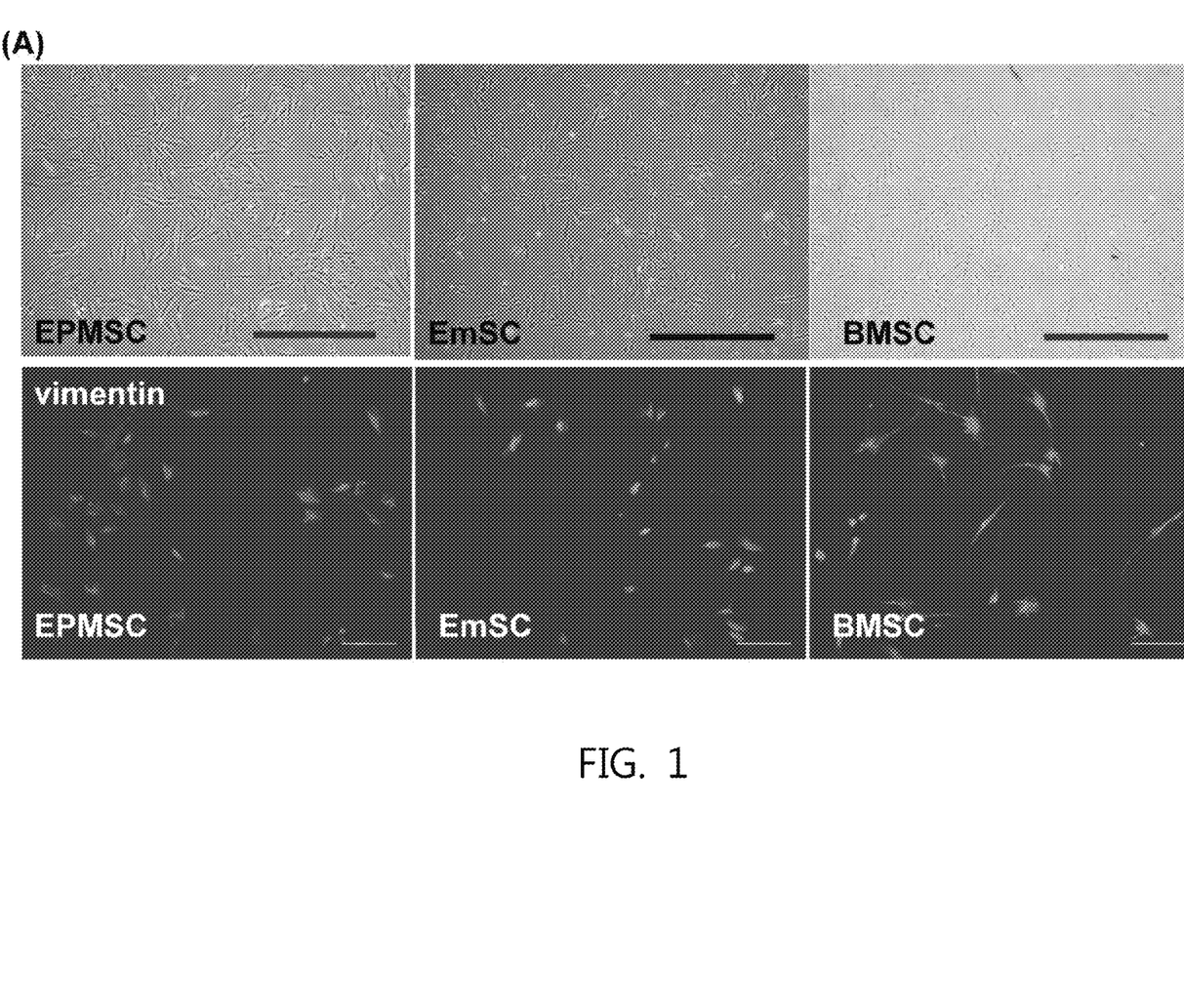
FIG. 1A shows representative photographs of EPMSCs, EmSCs, and BMSCs grown in proliferation medium, wherein the lower panel shows a positive vimentin stain (represented mesenchymal cells) for all three cell types.
FIG. 1B is a chart showing the EPMSC proliferation rate in comparison with that of endometrial stromal cells and BMSCs, wherein data are expressed as mean±SD (*P<0.05. Scale bar=1000 μm. (upper panel), 200 μm (lower panel))

EPMSCs were successfully expanded as a monolayer culture in medium containing 10% FBS in tissue culture flasks (FIG. 1). After 7-14 days of neuronal differentiation, roughly 50% of the cells in the dish exhibited refractile cell body morphologies with extended neurite-like structures arranged into a network. The EPMSC-derived neuroglial cells were identified by immunostaining with specific antibodies against Nestin, Tuj-1, NF200, MAP-2 and GFAP.

To identify the specific genes expressed in un-differentiated and differentiated endometrial polyp stem cells, total RNA was extracted using RNEasy® (Qiagen, Germany) according to the manufacturer's instructions, and reverse transcription-polymerase chain reaction (RT-PCR) with specific primers (Table 1) was performed as described previously (Lee et al., 2004). Briefly, total RNA was collected with using TRIzol (Invitrogen, Carlsbad, Calif., USA), and complementary DNA was synthesized with using a SuperScript first-strand synthesis system (Invitrogen, USA). Complementary DNA was amplified by PCR using an AmpliTaq Gold Kit (Applied Biosystems, Foster City, Calif., USA). The PCR products were resolved on 2% agarose gels.

Expression of neural-specific genes (Nestin, Tuj-1, MAP-2 and GFAP) was demonstrated by RT-PCR analysis (referring to FIGS. 3C and 3D). FIG. 3D shows the semi-quantitative expression of various neuronal markers. Despite the high expression of Tuj-1 in BMSCs, the expression levels of other markers were almost the same for the three cells types.

TABLE 1

The RT-PCR and qRT-PCR primers used to characterize endometrial polyp stem cells (EPMSCs) before and after differentiation.

| Gene | Sense (5'-3') | Antisense (5'-3') | Annealing temperature (° C.) | Product size (bp) |
| --- | --- | --- | --- | --- |
| PPAR-r | SEQ ID NO: 1 | SEQ ID NO: 2 | 60 | 120 |
| Osteopontin | SEQ ID NO: 3 | SEQ ID NO: 4 | 60 | 150 |
| Tuj-1 | SEQ ID NO: 5 | SEQ ID NO: 6 | 55 | 559 |
| GFAP | SEQ ID NO: 7 | SEQ ID NO: 8 | 60 | 132 |
| MAP2 | SEQ ID NO: 9 | SEQ ID NO: 10 | 55 | 192 |
| Nestin | SEQ ID NO: 11 | SEQ ID NO: 12 | 60 | 167 |
| TERT | SEQ ID NO: 13 | SEQ ID NO: 14 | 55 | 185 |
| GAPDH | SEQ ID NO: 15 | SEQ ID NO: 16 | 60 | 136 |

Colony-Forming Assays and the Spheroid-Forming Assay

To compare the clonogenicity of EPMSCs, EmSCs and BMSCs, a colony-forming unit fibroblast (CFU-F) assay was performed. The endometrial polyp stem cells were seeded at a clonal density of 250-300 cells/cm$^2$ on 60-mm fibronectin-coated dishes (Becton, Dickinson, USA), and cultured in DMEM-LG supplemented with 10% FCS, 100 mg/mL penicillin G sodium, and 100 mg/mL streptomycin sulfate. Cells were incubated at 37° C. in 5% $CO_2$. The medium was changed every 3-4 days. After 14 days, cells were fixed with 4% paraformaldehyde for 10 min at room temperature and stained for 2 h with 0.5% Toluidine Blue. The dish was then washed and dried, and colony formation was evaluated macroscopically. Colonies were defined as containing >50 cells microscopically. After counting colonies, colony-forming efficiency was calculated by dividing the average number of colonies by 100 cells. A spheroid was generated using suspension culture in ultra-low-attachment dishes (cat. No. 3471; Corning, Mass., USA). Stem cells from endometrial polyps, the endometrium, and bone marrow were released from monolayer cultures with 0.5% trypsin/2 mM EDTA, resuspended in complete media, transferred to ultra-low-attachment wells at 5,000 cells/well, and incubated for 48 h at 37° C.

Figure 4:
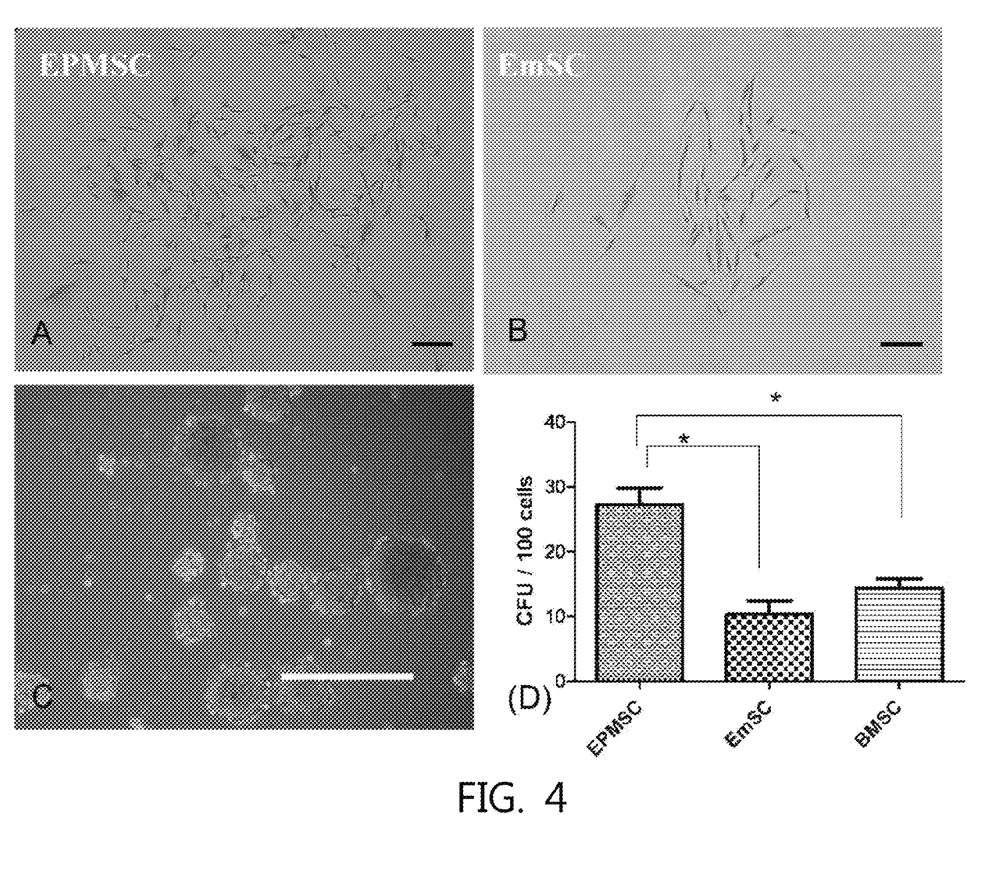
FIG. 4A and FIG. 4B show representative colonies in EPMSCs and EmSCs.
FIG. 4C shows spheroid formation under suspension culture in low-attachment dishes.
FIG. 4D is a chart showing proportion of CFU within BMSC, EPMSC and EmSC populations, wherein data are expressed as mean±SD (*P<0.005. Scale bar=100 μm (A, B), 1000 μm (C))

Referring to FIGS. 4A to 4D, the CFU-F capacity (clonogenicity) of EPMSCs (27%) was higher than that of EmSCs (9.4%), and BMSCs (14.9%). The EPMSCs easily formed a stem-cell-like spheroid morphology under low-attachment culturing in dishes as shown in FIG. 4C.

Quantitative RT-PCR of the TERT Gene and Other Differentiation Marker Genes (PPARr, Osteopontin)

For quantitative RT-PCR (qRT-PCR) analysis of telomerase reverse transcriptase (TERT), FastStart universal SYBR green master (ROX, Roche, USA) gene expression assays were performed in an ABI step one plus system (Applied Biosystems, USA), with glyceraldehyde 3-phosphate dehydrogenase (GAPDH) used as an internal control. Table 1 shows sequences of primers and annealing temperatures.

Figure 5:
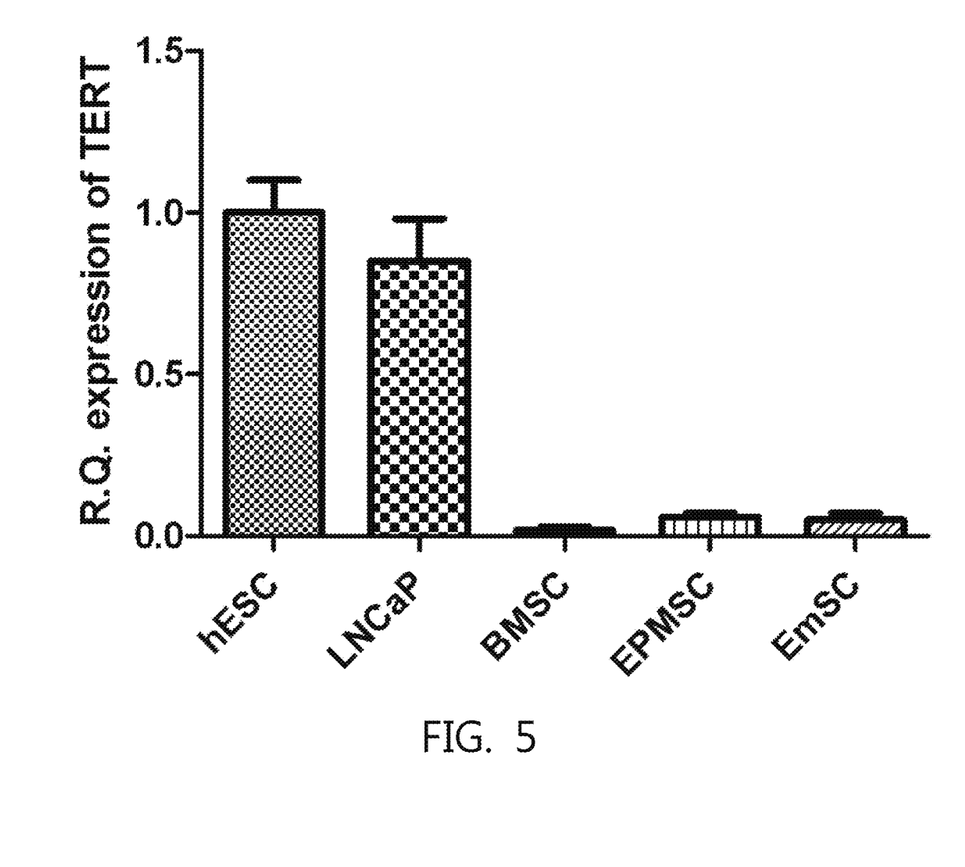
FIG. 5 is a chart showing the qRT-PCR results comparing relative TERT gene expression levels in EPMSCs, EmSCs, BMSCs, human embryonic stem cells and human cancer cells (LNCaP), wherein the quantification (R. Q.) of TERT expression relative to the expression level of hESCs is taken as 1, and error bars represent standard deviation (SD).

Referring to FIG. 5, TERT expression was much lower than that in human embryonic stem cells and cancer cells (LNCaP). Statistical analysis herein was performed using SPSS software (SPSS, Chicago, Ill., USA). Values are expressed as means±SD. The one-way ANOVA test and Bonferroni correction were used for multiple comparisons. A value of $p<0.05$ was considered statistically significant.

In the present invention, endometrial polyps are the rich source of mesenchymal stem cells. Notably, EPMSCs have a proliferation rate and colony-forming capacity exceeding those of MSCs derived from the endometrium and bone marrow. The EPMSCs also have a differentiation ability exceeding that of MSCs derived from the endometrium.

In the present invention, it has been found that EPMSCs have therapeutic potential. Cell replacement therapies have significant promise in the skeletal and nervous systems, where transplanted stem cells have been shown to promote functional recovery in animal models (Ding et al., 2006, 2007a, 2007b). Heterologous transplantation accompanying immunosuppression is a potential problem. EPMSCs can be generated autologously and are an accessible adult tissue source. Otherwise, a heterologous transplantation with MHC matching is needed. The EPMSCs can readily generate mesenchymal and neural cells types, have good clonogenicity and, thus, are a potential solution to these problems.

In terms of expansion potential, EPMSCs proliferate more rapidly than BMSCs and EmSCs. Additionally, EPMSCs can be more easily induced to differentiate into a variety of mesenchymal lineages than EmSCs, and have the same differentiation potential as BMSCs. In terms of the clonal assay, which determines the capacity to identify colony-forming stromal cells (Schwab et al., 2008), EPMSCs had better colony formation ability than both BMSCs and EmSCs.

In summary, the present invention has disclosed that a multipotent adult precursor cell resembling BMSCs can be isolated and expanded from endometrial polyps. In other words, EPMSCs may be an alternative adult stem cell resource for regenerative tissue repair.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

The invention claimed is:

1. A formulation comprising: an endometrial polyp stem cell, which is isolated from an endometrial polyp tissue wherein the endometrial polyp stem cell expresses vimentin, CD13, CD29, CD44, and CD90, and has TERT expression statistically significantly lower than a human embryonic stem cell or a cancer cell, and an osteogenic medium comprising dexamethasone, β-glycerol phosphate, and ascorbate.

2. The formulation of claim 1, wherein the endometrial polyp stem cell has no expression of CD3, CD34, and CD45.

3. The formulation of claim 1, wherein the endometrial polyp tissue is obtained from endometrium of a hysterectomy specimen.

4. The formulation of claim 1, wherein the endometrial polyp stem cell has clonogenicity.

* * * * *

SEQUENCE LISTING

```
<160> NUMBER OF SEQ ID NOS: 16

<210> SEQ ID NO 1
<211> LENGTH: 21
<212> TYPE: DNA
<213> ORGANISM: human

<400> SEQUENCE: 1
agcctcatga agagccttcc a                                                   21

<210> SEQ ID NO 2
<211> LENGTH: 19
<212> TYPE: DNA
<213> ORGANISM: human

<400> SEQUENCE: 2
tccggaagaa acccttgca                                                      19

<210> SEQ ID NO 3
<211> LENGTH: 18
<212> TYPE: DNA
<213> ORGANISM: human

<400> SEQUENCE: 3
aggaggaggc agagcaca                                                       18

<210> SEQ ID NO 4
<211> LENGTH: 20
<212> TYPE: DNA
<213> ORGANISM: human

<400> SEQUENCE: 4
ctggtatggc acaggtgatg                                                     20

<210> SEQ ID NO 5
<211> LENGTH: 22
<212> TYPE: DNA
<213> ORGANISM: human

<400> SEQUENCE: 5
gtcagctcaa tgccgacctc cg                                                  22

<210> SEQ ID NO 6
<211> LENGTH: 21
<212> TYPE: DNA
<213> ORGANISM: human

<400> SEQUENCE: 6
gcagtggcgt cctggtactg c                                                   21

<210> SEQ ID NO 7
<211> LENGTH: 17
<212> TYPE: DNA
<213> ORGANISM: human
```

```
<400> SEQUENCE: 7
agggctgaca cgtccac                                                  17

<210> SEQ ID NO 8
<211> LENGTH: 19
<212> TYPE: DNA
<213> ORGANISM: human

<400> SEQUENCE: 8
gccttagagg ggagaggag                                                19

<210> SEQ ID NO 9
<211> LENGTH: 18
<212> TYPE: DNA
<213> ORGANISM: human

<400> SEQUENCE: 9
gcatgagctc ttggcagg                                                 18

<210> SEQ ID NO 10
<211> LENGTH: 22
<212> TYPE: DNA
<213> ORGANISM: human

<400> SEQUENCE: 10
ccaattgaac ccatgtaaag cc                                            22

<210> SEQ ID NO 11
<211> LENGTH: 21
<212> TYPE: DNA
<213> ORGANISM: human

<400> SEQUENCE: 11
gaaacagcca tagagggcaa a                                             21

<210> SEQ ID NO 12
<211> LENGTH: 23
<212> TYPE: DNA
<213> ORGANISM: human

<400> SEQUENCE: 12
tggttttcca gagtcttcag tga                                           23

<210> SEQ ID NO 13
<211> LENGTH: 20
<212> TYPE: DNA
<213> ORGANISM: human

<400> SEQUENCE: 13
agctatgccc ggacctccat                                               20

<210> SEQ ID NO 14
<211> LENGTH: 20
<212> TYPE: DNA
<213> ORGANISM: human

<400> SEQUENCE: 14
gcctgcagca ggaggatctt                                               20

<210> SEQ ID NO 15
<211> LENGTH: 19
<212> TYPE: DNA
```

```
<213> ORGANISM: human

<400> SEQUENCE: 15
ggcagcagca agcattcct                                          19

<210> SEQ ID NO 16
<211> LENGTH: 18
<212> TYPE: DNA
<213> ORGANISM: human

<400> SEQUENCE: 16
gcccaacacc cccagtca                                           18
```